United States Patent [19]

Quay et al.

[11] Patent Number: 4,863,716
[45] Date of Patent: Sep. 5, 1989

[54] DETERMINATION OF FALLOPIAN TUBAL PATENCY BY MAGNETIC RESONANCE IMAGING

[75] Inventors: Steven C. Quay, Los Altos Hills; Scott M. Rocklage, Saratoga, both of Calif.

[73] Assignee: Salutar, Inc., Sunnyvale, Calif.

[21] Appl. No.: 58,180

[22] Filed: Jun. 4, 1987

Related U.S. Application Data

[63] Continuation-in-part of Ser. No. 47,614, May 8, 1987, and a continuation-in-part of Ser. No. 47,584, May 8, 1987.

[51] Int. Cl.⁴ .............................................. A61K 49/00
[52] U.S. Cl. ....................................... 424/9; 128/653; 128/654; 436/173; 436/806
[58] Field of Search ................... 128/654, 653; 424/9; 436/173, 806

[56] References Cited

U.S. PATENT DOCUMENTS

| | | | |
|---|---|---|---|
| 4,637,929 | 1/1987 | Quay | 424/9 |
| 4,647,447 | 3/1987 | Gries et al. | 424/9 |
| 4,687,658 | 8/1987 | Quay | 424/9 |
| 4,687,659 | 8/1987 | Quay | 424/9 |

*Primary Examiner*—Robert J. Warden
*Assistant Examiner*—Robert Benson
*Attorney, Agent, or Firm*—William B. Walker

[57] ABSTRACT

This invention is a method for obtaining improved NMR images of the uterine cavity and fallopian tubes comprising imjecting a physiologically acceptable solution of a chelate of a parmagnetic material into the uterus under sufficient pressure to cause the solution to pass through the fallopian tubes and obtaining an enhanced NMR image of the tissue surrounding the fallopian tubes. The chelates and the injection solutions thereof do not include carbohydrate groups or other compounds which might support growth of *Staphylococcus aureus* or other pathological miroorganisms in the peritoneal cavity.

Kits including contrast medium and non-metallic uterine balloon catheters suitable for use with NMRI procedures are also included within the scope of this invention.

10 Claims, No Drawings

DETERMINATION OF FALLOPIAN TUBAL PATENCY BY MAGNETIC RESONANCE IMAGING

RELATIONSHIP TO COPENDING APPLICATIONS

This application is a continuation-in-part of copending applications Ser. No. 47,614 filed May 8, 1987 and Ser. No. 47,584 filed May 8, 1987.

FIELD OF THE INVENTION

This invention relates to the use of magnetic resonance imaging (MRI) contrast agents to provide a superior image of internal body cavities. In particular this invention relates to a method for obtaining a superior image of the cervical cavity and fallopian tubes to determine the presence of abnormalities causing infertility, using NMR imaging with contrast agents providing a superior definition.

BACKGROUND OF THE INVENTION

Magnetic resonance imaging (NMRI) is a diagnostic technique which produces high resolution images of internal organs without using ionizing radiation. In forming these images, the nuclei of hydrogen atoms (the most abundant element in the body, largely in the form of $H_2O$) are first aligned with a large magnetic field, then excited with a radiofrequency (Rf) pulse to induce flipping of the nuclei and orientation against the field, and finally, detection of the emitted Rf signal during the reorientation process which occurs after the cessation of the Rf pulse. The strength and rate of change in the strength of the emitted signals depend upon the number of nuclei involved and the characteristic relaxation times (spin-lattice relaxation times or $T_1$ and spin-spin relaxation times or $T_2$) associated with the chemical surroundings of the nuclei. By applying small magnetic field gradients to a volume of material and changing the direction of these gradients, spatial information can be decoded from the signal. Mathematical manipulation then allows construction of an image on a cathode ray tube in a manner similar to data from X-ray computed tomography (CT). The radiofrequency radiation employed is well below that of X-rays, is non-ionizing, and is considered to be incapable of causing any damage to molecules of living cells. There is a small amount of tissue heating which is believed to be clinically insignificant.

Cervical malformations, malpositions and tumors do not often interfere with conception, but they may be a factor in faulty nidation and early abortion. Submucous myomas may obstruct the uterine ends of the tube and thus prevent fertilization or may distort the uterine cavity and interfere with nidation. Partial or complete occlusion of the fallopian tubes is an important etiological factor in infertility, encountered in about 30% of all women who fail to conceive. Tubal obstruction usually results from the destructive effect of pathogenic microorganisms on the mucosal surface. Gonorrheal salpingitis is an important cause of obstruction or restriction, but not the only one. Bacteria regularly ascend from the infected uterine cavities of women who have aborted or have had a normal delivery, and may produce a destructive endosalpingitis. Uterine fibroids or cornual adenomyosis may distort and occlude the uterine ends of the tubes. The tubes can also be kinked or occluded by adhesions after appendicitis or other infections or areas of pelvic endometriosis. Sometimes, intermittent obstruction occurs because of spasm of the uterine ends of the tubes.

Procedures for examining for fallopian tubal patency include uterotubal insufflation (Rubin's test), injecting a gas such as carbon dioxide into the uterine cavity under pressure and recording the alterations in pressure can detect total blockage of the tubes. Hysterosalipingography (HS) employs X-ray visualization of the uterine cavity and the tubal lumina after the injection of an opaque dye into the upper genital tract. Pneumohysterosalpingography (PHS) is similar to HS but uses X-ray imaging during sequential insufflation with gas and with an opaque dye. Laparoscopy involves direct observation of the passage of dye from the ends of the fallopian tubes through optical devices inserted through small incisions in the abdominal area. Culdoscopy is similar to laparoscopy, but the optical device is inserted through an incision in the vaginal vault.

Rubin's test has fallen into disuse, and techniques providing more information have been developed. The best current method involves the invasive techniques of laparoscopy and culdoscopy using a dye such as methylene blue. These require anesthesia and surgical procedures, with attendant risks.

Hysterosalpingography and PHS avoid the use of anesthia and surgery. They require the injection of a radiopaque dye through the cervix uteri and monitoring by fluoroscope and film to provide a permanent record of the shape of the uterine cavity and fallopian tubes. However, despite development of faster procedures and use of lower levels of X-rays, the radiation dosage to which the ovaries are exposed during this procedure are believed to provide a serious risk of genetic damage and birth defects. Muller, H. in *Am. J. Obstet. Gynecol.* 67: 463 (1954) has stated in regard to irradiation of the gonads that there is "no dose so small as to give no mutations at all; each individual ionization and probably each activation of an atom carries its definite chance of producing a mutation." Sheikh, H. et al in *Am. J. Obstet. Gynecol*, 124(3): 307–310 states that, "On the average, each newly mutated gene, no matter how small the detriment it occasions, eventually takes its toll in the form of making a major contribution to the extinction of the line of descent." Furthermore, these procedures are not easily susceptible to tomographic analysis.

Ultrasound and CT have been applied to examine the pelvic area including the cervix and ovaries. The lack of definition in ultrasound methods renders them useless in determining the presence of obstructions or other endothelial deformations of the fallopian tubes. CT methods are limited by the inability to distinguish between soft materials having closely similar X-ray absorption characteristics. They are also subject to distortion due to metal clips, contrast media and bone density. As a result, neither of these procedures are used in determination of fallopian tubal patency.

More recently, NMRI techniques are being developed for imaging the pelvic regions. Hamlin, D. et al, *AJR*. 145: 585–590 (1985) reports the study of ovarian masses in patients using NMRI. McCarthy, S. in *Magnetic Resonance Imaging*, 4:59–66 (1986) indicates the uterine fundus, isthmus, cervix and vagina are easily identified in NMRI. The ovaries appear as medium intensity structures, with increase in intensity with $T_2$, blending with fat. Follicles can be accentuated on long TR, TE sequences. Hricak, H. in *AJR*. 146: 1115–1122

(1986) using the 0.35 T MT/S system of DIASONICS (Milpitas, CA) reported that normal ovaries were most difficult to demonstrate on NMRI. While more recent improved machines have reduced these difficulties, most advance imaging equipment and methods do not provide an image of fallopian tubes with sufficient contrast and detail to determine patency. Ovaries and fallopian tubes have a low to medium signal intensity on the $T_1$-weighted image (short TR and TE). When TR is short, distinguished ovaries from the surrounding bowel is difficult. When TR is longer, ovarian signal intensity increases and approaches that of the surrounding fat.

Prior to this invention, the image definition available with most advanced NMRI procedures and equipment was unable to provide the definition required to evaluate fallopian tubal patency.

DESCRIPTION OF THE PRIOR ART

Image definition in ultrasound has been improved by injecting a viscous dextran in sterile aqueous dextrose solution or sterile water-saline into the cervix and fallopian tubes using a Harris Uterine Injector (balloon catheter) as described by Richman, et al, *Radiology*, 152: 507-510 (1984). The aqueous solution provides a difference in density absorption characteristics which can be differentiated by the ultrasound imaging. Use of opaque solutions to improve contrast in hysterosalping-ograpy is also customary as described by Richman. In this procedure, the iodine-containing solutions are opaque to X-rays, providing a contrast with the surrounding tissue.

The use of suspensions of ferromagnetic particles as contrast media in NMRI is described in PCT application WO 85/04330. This publication notes the use of paramagnetic contrast media in some NMRI procedures but teaches that no NMR contrast agents are available which are capable of selectively enhancing contrast between different tissue types in the $T_2$ image. The ferromagnetic particles contain atoms which, within volumes called domains, have their magnetic moments (resulting from their unpaired electrons) aligned. Ferromagnetism, in contrast to paramagnetism, is a cooperative phenomenon and can only exist in aggregations of atoms, that is, particles. Injection of ferromagnetic particle suspensions such as cellulose derivatives into the bladder, uterus, billiary duct or parotid duct in aqueous solutions containing viscosity increasing substances is suggested. Administration into body sites from which the contrast agent may be discharged from the body without passing through body tissue is advised. It may be noted that suspensions injected into the fallopian tubes pass through the tubes into the peritoneal cavity and require passage through body tissue for discharge. It may also be noted that cellulose derivatives support bacterial growth, and if injected into the peritoneal cavity through the fallopian tubes, could increase risk of *Staphylococcus aureus* infections and Toxic Shock Syndrome. Furthermore, ferromagnetic particles suspensions, which provide greatly reduced signal intensity due to $T_2$ shortening and magnetic susceptibility effects, could not be visualized within the cavity of the fallopian tube, and would thus fail to provide information about tubal patency.

The use of water-soluble hydroxy group-containing polymerized carbohydrates or polymerized sugar alcohols and their derivatives chemically bound to paramagnetic materials in ultrasound and NMR procedures is described in European Patent Application No. 186947. The paramagnetic metals can have atomic numbers of 21-29, 42, 44, 57-70, for example, Gd, Er, Eu, Dy, Ho, Mn, Fe, Ni, Cr or Cu. The metal can be in the form of a chelate complex bound to the hydroxylated polymer. Compounds which are not degraded by the body are recommended for use for examination of the gastrointestional tract, bladder and uterus in applications where they need not pass through the body, excluding applications to the fallopian tubes, as noted above. The carrier can also include a viscosity enhancer and/or osmolality regulator. The carbohydrate and sugar alcohol polymer derivatives of this patent could support bacterial growth, and if injected into the fallopian tubes, could increase risk of *Staphylococcus aureus* infections and Toxic Shock Syndrome. These compounds are thus entirely unsuitable for use in determining fallopian tubal patency.

SUMMARY OF THE INVENTION

This invention is a method for obtaining improved NMR images of the uterine cavity and fallopian tubes comprising injecting a physiologically acceptable solution of a chelate of a paramagnetic material into the uterus under sufficient pressure to cause the solution to pass through the fallopian tubes and obtaining an enhanced NMR image of the tissue surrounding the fallopian tubes. The chelates and the injection solutions thereof do not include carbohydrate groups or other compounds which might support growth of *Staphylococcus aureus* or other pathological microorganisms in the peritonea cavity.

Kits including contrast medium and non-metallic uterine balloon catheters suitable for use with NMRI procedures are also included within the scope of this invention.

DETAILED DESCRIPTION OF THE INVENTION

The method of this invention for improved NMR imaging of the uterus and fallopian tubes comprises injecting solution of a tubal patency NMRI contrast agent into the uterine cavity under sufficient pressure to cause the liquid to pass into the fallopian tubes, the solution and the chelate dissolved therein being physiologically acceptable for injection into the peritoneal cavity through the cervix and fallopian tubes. The uterine and fallopian tube surfaces are then imaged using NMRI procedures.

The liquid injected into the uterine cavity comprises a physiologically suitable paramagnetic metal ion containing chelate dispersed in a physiologically acceptable oil or aqueous solution containing excipients such as surfactants and/or viscosity increasing substances.

Because the fallopian tubes, peritoneal cavity and internal system are exposed to the contrast medium in the method of this invention, the metal ion chelates and the solutions should satisfy "physiologically suitable" and "physiologically acceptable" criteria in the context of this invention. A summary of preferred requirements are set forth below.

The metal ion chelate must have a safe effective dose to lethal dose ratio ($LD_{50}/ED_{50}$) of greater than 10 and preferably greater than 50.

The metal ion chelates and the injection liquid in which they are dissolved preferably are free from significant quantities of compounds and other materials which would increase the risk of *Staphylococcus aureus* infections or the release of toxic shock syndrome toxin- 1 (TSST-1) or other toxins into the peritoneal cavity. Toxic shock syndrome (TSS) is a clinical entity characterized by hypotension, fever, hyperemia of mucous membranes, erythroderma with subsequent desquamation, and multisystem involvement. Certain strains of *S. aureus* have been found to cause this illness, and identification of TSST-1 and other possible toxins produced by this strain is reported by Garbe, P. et al, JAMA. 253(17): 2538–2542 (1985). Tryptophane auxotypy has been reported with this strain by Chu, M. et al, *J. Infect. Dis.* 151(6): 1157 (1985), and toxin concentration increases in the presence of low $Mg^{+2}$ ion concentrations have been reported with this strain by Mills, J. et al, *J. Infect. Dis.* 151(6): 1158 (1985). Other details about this frequently fatal disease have been reported by De Azavedo, J. et al, *Infect. Immun.* 46(2): 314–317 (1984); Rasheed, J. et al, *Infect. Immun.* 47(3): 598–604 (1985); Schlievert, P. et al, *Obstet. Gynecol.* 64: 666–671 (1984); and Tierno, P. et al, *Contraception.* 31(2): 185–194 (1985). Chelates and excipients such as thickeners which would support microbial growth, such as carbohydrates and similar materials would therefore be unsuitable and are excluded by the definition of physiologically suitable or physiologically acceptable for use in tubal patency tests.

Other features of microbial physiology are important in selecting suitable contrast agents among the paramagnetic chelate complexes which are capable of modifying the magnetic resonance signal. With some bacteria, notably *Neisseria meningitidis* (Claver, G. et al, *Infect. Immun.* 25: 880–890 (1979)), *Neisseria gonorrhoeae* (Finkelstein, R. et al, *Infect. Immunol.* 32: 609–613 (1981)) and a mutant form of *Salmonella typhimurium* defective in catechol synthesis (Jones, R. *Nature (London)*, 267: 63–64 (1977)), certain chelators such as desferrioxamine may afford a degree of protection against infection. Recognition of this fact prompted Calver et al to suggest that desferrioxamine may have a chemotherapeutic role in severe neisserial disease (Carver, G. et al, supra).

The peritoneal cavity is sensitive to irritation, and the metal ion chelate and injection solution should not cause undue irritation. A conventional test for irritation is the rabbit eye irritation test wherein the medium is placed in the conjunctival sac of one eye of a series of rabbits, and the presence and degree of irritation is observed.

Because of the exposure of the fallopian tube surfaces and ovary ducts to the contrast medium, and because the materials pass into the peritoneal cavity and into the internal system, the metal ion chelates and other solution components useful in the method of this invention are preferably free from all mutagens. In general, any test or combination of tests is suitable if it will detect many types of genetic damage, detect metabolites as mutagens, detect DNA damage, detect mammalian point mutations, and be suitable for broad spectrums of chemical classes. Examples of tests which are customarily used to determine the potential for mutagenicity are the Ames Test Salmonella typhimurium, Micronucleus test with the mouse or the In Vitro Chromosomal Aberration Assay in Chinese Hamster Ovary Cells, Rat Hepatocyte Primary Culture/DNA Repair Test, and Mammalian Cell Forward Gene Mutation Assay.

The metal ion chelate and other solution components useful in the method of this invention are also preferably free from reproduction and fertility effects. The freedom from adverse reproductive effects can be determined by one or more of the following standard tests: Two Generation Reproduction and Fertility Studies using rats to provide information concerning the effects of the chelates and solution on gonadal function, conception, parturition and the growth and development of the offspring; Male and Female Fertility Tests using rate; and Perinatal and Postnatal Studies with rats, evaluating the effects of the chelates and solutions upon duration of gestation, normal parturition, and litter effects when given during the last one-third of gestation and continued through lactation and weaning, and the like.

The metal ion chelates and solutions should also be free of teratogens. Freedom from embryotoxic and teratogenic effects can determined by administering the contrast medium to pregnant female rats, mice, hamsters and/or rabbits during the gestational period of organogenesis, and the fetuses are removed and examined for viseral anomalies and skeletal defects.

The paramagnetic metal ions of the complexes preferably are divalent or trivalent ions of elements with an atomic number of 21 to 29, 42, 44 and 58 to 70. Suitable ions include chromium(III), manganese(II), iron(III), iron(II), cobalt(II), nickel(II), copper(II), praseodymium(III), neodymium(III), samarium(III), ytterbium(III), gadolinium(III), terbium(III), dysprosium(III), holmium(III) and erbium(III).

These metal ions should be held tightly in metal complexes or chelates which have the physical properties required for incorporation into the desired liquid injection composition. A wide variety of metal ion chelates have been suggested for general use in NMRI procedures.

One example of suitable contrast agents are ferrioxamine-paramagnetic contrast agents, paramagnetic metal ion salts of FOM-A described in U.S. Pat. No. 4,637,929. FOM is at least one member of the ferrioxamine family of chelates consisting of A, B, C, D1, D2, E and F, which has a paramagnetic atom of ionized Fe chelated therein at a plurality of coordination points to chemically isolate the Fe ion from the in vivo environment. A is hydrogen or an amide group of the formula:

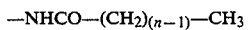

$$-NHCO-(CH_2)_{(n-1)}-CH_3$$

wherein n is an integer of from 1 to 18. A preferred paramagnetic metal ion salt of this type is the ferric coordination compound of the mesylate salt of desferrioxamine, such as ferric N-(5-(3-((5-aminopentyl)-hydroxycarbamoyl)propionamido)pentyl)-3-((5-(N-hydroxyacetamido)pentyl)carbamoyl)propionhydroxamic acid monomethanesulfonate salt.

Suitable dipyridoxyl phosphate chelates are described in our copening Application Ser. No. 47,614 filed May 8, 1987, the entire contents of which are hereby incorporated by reference. They are chelates of the compositions of Formula I and their salts:

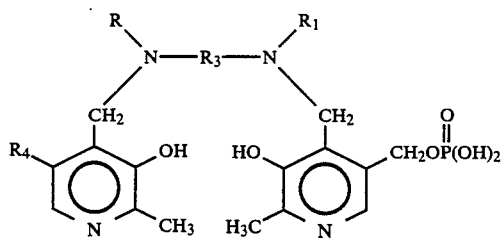

wherein,
R is hydrogen or

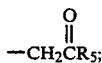

$R_1$ is hydrogen or

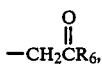

and one of R and $R_1$ is other than hydrogen;
$R_3$ is alkylene having from 1 to 8 carbons, 1,2-cycloalkylene having from 5 to 8 carbons, or 1,2-arylene having from 6 to 10 carbons, and
$R_4$ is hydrogen, alkyl having from 1 to 6 carbons or

$R_5$ and $R_6$ are each, individually, hydroxy, alkoxy having from 1 to 18 carbons, hydroxy-substituted alkoxy having from 1 to 18 carbons, amino or alkylamino having from 1 to 18 carbons.

The phosphate group mono and diesters with mono and polyhydric alkanols having from 1 to 18 carbons, or alkylamino alcohols, each having from 1 to 18 carbons, and the salts of the above compounds are included within the scope of this invention.

The preferred chelates of the compounds of Formula I and salts and esters thereof are with paramagnetic metal ions having atomic numbers of from 21–29, 42, 44 and 58–70, and optimally manganese(II) and gadolinium(III).

In Formula I, $R_5$ and $R_6$ are preferably each individually hydroxy, alkoxy having from 1 to 8 carbons, ethylene glycol, glycerol, amino or alkylamino having from 1 to 8 carbons. Optimally, $R_5$ and $R_6$ are hydroxy and the salts thereof.

The terms "alkyl" and "alkylene", as used herein, include both straight and branch-chained, saturated and unsaturated hydrocarbons. The term "1,2-cycloalkylene" includes both cis and trans cycloalkyl groups and alkyl substituted cycloalkylene groups bonded at the 1,2-positions to respective nitrogen atoms and alkyl substituted derivatives thereof having from 5 to 8 carbons. The term "1,2-arylene" includes phenyl and naphthyl groups bonded at the 1,2-positions to respective nitrogen atoms and alkyl substituted derivatives thereof, having from 6 to 10 carbons.

The compound, N,N'-bis-(pyridoxal-5-phosphate)-ethylenediamine-N,N'-diacetic acid is referred to hereinafter as DPDP, and the manganese(II) chelate is referred to hereinafter as Mn(DPDP). The compound N,N'-bis(pyridoxal-5-phosphate)-trans-1,2-cyclohexyl-diamine-N,N'-diacetic acid is referred to hereinafter as DPCP, and the manganese(II) chelate is referred to hereinafter as Mn(DPCP).

Other suitable chelating compounds of Formula I include
N,N'-bis(pyridoxal-5-phosphate)-1,3-(n-propylene)-N,N'-diacetic acid,
N,N'-bis(pyridoxal-5-phosphate)-1,2-(n-propylene)-N,N'-diacetic acid,
N,N'-bis(pyridoxal-5-phosphate)-1,2-isopropylene-N,N'-diacetic acid,
N,N'-bis(pyridoxal-5-phosphate)-1,2-(n-butylene)-N,N'-diacetic acid,
N,N'-bis(pyridoxal-5-phosphate)-1,4-(n-butylene)-N,N'-diacetic acid,
N,N'-bis(pyridoxal-5-phosphate)-1,3-(n-butylene)-N,N'-diacetic acid,
N,N'-bis(pyridoxal-5-phosphate)-1,2-(3-methylene)-propyl-N,N'-diacetic acid,
N,N'-bis(pyridoxal-5-phosphate)-trans-1,2-cyclopentylenediamine-N,N'-diacetic acid,
N,N'-bis(pyridoxal-5-phosphate)-trans-1,2-cycloheptylenediamine-N,N'-diacetic acid,
N,N'-bis(pyridoxal-5-phosphate)-trans-1,2-cyclooctylenediamine-N,N'-diacetic acid,
N,N'-bis(pyridoxal-5-phosphate)-1,2-phenylenediamine-N,N'-diacetic acid,
N,N'-bis(pyridoxal-5-phosphate)-cis-1,2-cyclohexylenediamine-N,N'-diacetic acid,
N,N'-bis(pyridoxal-5-phosphate-(N-methylethanolamine)monoester)ethylenediamine-N,N'-diacetic acid,
N,N'-bis(pyridoxal-5-phosphate(N-methylethanolamine)monoester)-1,3-(n-propylene)diamine-N,N'-diacetic acid,
N,N'-bis(pyridoxal-5-phosphate(N-methylethanolamine)monoester)-1,2-(n-propylene)diamine-N,N'-diacetic acid,
N,N'-bis(pyridoxal-5-phosphate(N-methylethanolamine)monoester)-1,2-isopropylenediamine-N,N'-diacetic acid,
N,N'-bis(pyridoxal-5-phosphate(N-methylethanolamine)monoester)-1,2-(n-butylene)diamine-N,N'-diacetic acid,
N,N'-bis(pyridoxal-5-phosphate(N-methylethanolamine)monoester)-1,4-(n-butylene)diamine-N,N'-diacetic acid,
N,N'-bis(pyridoxal-5-phosphate(N-methylethanolamine)monoester)-1,3-(n-butylene)diamine-N,N'-diacetic acid,
N,N'-bis(pyridoxal-5-phosphate(N-methylethanolamine)monoester)-1,2-(3-methyl)-propylenediamine-N,N'-diacetic acid,
N,N'-bis(pyridoxal-5-phosphate(N-methylethanolamine)monoester)-trans-1,2-cyclohexylenediamine-N,N'-diacetic acid,
N,N'-bis(pyridoxal-5-phosphate(N-methylethanolamine)monoester)-trans-1,2-cyclopentylenediamine-N,N'-diacetic acid,
N,N'-bis(pyridoxal-5-phosphate(N-methylethanolamine)monoester)-trans-1,2-cycloheptylenediamine-N,N'-diacetic acid,
N,N'-bis(pyridoxal-5-phosphate(N-methylethanolamine)monoester)-trans-1,2-cyclooctylenediamine-N,N'-diacetic acid, N,N'-bis(pyridoxal-5-phosphate(N-methyle-thanolamine)monoester)-1,2-phenylenediamine-N,N'-diacetic acid, N,N'-bis(pyridoxal-5-phosphate(N-methyle-thanolamine)monoester)-cis-1,2-cyclohexylenedia-mine-N,N'-diacetic acid, N,N'-bis-(pyridoxal-5-phosphate)ethylenediamine-N-acetic acid, N,N'-bis(pyridoxal-5-phosphate)-1,3-(n-propylene)-diamine-N-acetic acid, N,N'-bis(pyridoxal-5-phosphate)-1,2-(n-propylene)-diamine-N-acetic acid, N,N'-bis(pyridoxal-5-phosphate)-1,2-iso-propylenediamine-N-acetic acid, N,N'-bis(pyridoxal-5-phosphate)-1,2-(n-butylene)dia-mine-N-acetic acid, N,N'-bis(pyridoxal-5-phosphate)-1,4-(n-butylene)dia-mine-N-acetic acid, N,N'-bis(pyridoxal-5-phosphate)-1,3-(n-butylene)dia-mine-N-acetic acid, N,N'-bis(pyridoxal-5-phosphate)-1,2-(3-methyl)-propylenediamine-N-acetic acid, N,N'-bis(pyridoxal-5-phosphate)-trans-1,2-cyclohex-ylenediamine-N-acetic acid, N,N'-bis(pyridoxal-5-phosphate)-trans-1,2-cyclopen-tylenediamine-N-acetic acid, N,N'-bis(pyridoxal-5-phosphate)-trans-1,2-cyclohep-tylenediamine-N-acetic acid, N,N'-bis(pyridoxal-5-phosphate)-trans-1,2-cyclooc-tylenediamine-N-acetic acid, N,N'-bis(pyridoxal-5-phosphate)-1,2-phenylenedia-mine-N-acetic acid, N,N'-bis(pyridoxal-5-phosphate)-cis-1,2-cyclohex-ylenediamine-N-acetic acid, and N-pyridoxal-N'-(pyridoxal-5-phosphate)ethylenedia-mine-N,N'-diacetic acid (DPMP).

Manganese chelates of PLED analogs and derivatives are described in our copening application filed May 8, 1987 U.S. Ser. No. 47,584, the entire contents of which is hereby incorporated herein by reference. This group of chelates are chelates of the compounds of Formula II and their water-soluble salts:

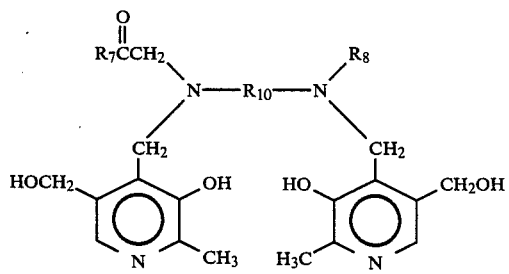

(II)

wherein, $R_7$ is hydroxy, alkoxy having from 1 to 18 carbons, hydroxy-substituted alkoxy having from 1 to 18 carbons, amino or alkylamido having from 1 to 18 carbons;

$R_8$ is hydrogen or

$R_9$ is hydroxy, alkoxy having from 1 to 18 carbons, amino or alkylamido having from 1 to 18 carbons; and $R_{10}$ is alkylene having from 1 to 8 carbons, 1,2-cycloalkylene having from 5 to 8 carbons, or 1,2-arylene having from 6 to 10 carbons.

The preferred chelates of the compounds of Formula II such as N,N'-di(pyridoxyl)ethylenediamine-N,N'-diacetic acid (PLED) and salts and esters thereof are with paramagnetic metal ions having atomic numbers of from 21–29, 42, 44 and 58–70, and optimally manganese(II) and gadolinium(III).

Other suitable chelating compounds of Formula II include

N,N'-bis(pyridoxal)-1,3-(n-propylene)-N,N'-diacetic acid,

N,N'-bis(pyridoxal)-1,2-(n-propylene)-N,N'-diacetic acid,

N,N'-bis(pyrodoxal)-1,2-isopropylene-N,N'-diacetic acid,

N,N'-bis(pyridoxal)-1,2-(n-butylene)-N,N'-diacetic acid,

N,N'-bis(pyridoxal)-1,4-(n-butylene)-N,N'-diacetic acid,

N,N'-bis(pyridoxal)-1,3-(n-butylene)-N,N'-diacetic acid,

N,N'-bis(pyridoxal)-1,2-(3-methylene)propyl-N,N'-diacetic acid,

N,N'-bis-(pyridoxal)-trans-1,2-cyclohexylenedia-mine-N,N'-diacetic acid

N,N'-bis(pyridoxal)-trans-1,2-cyclopentylenedia-mine-N,N'-diacetic acid,

N,N'-bis(pyridoxal)-trans-1,2-cycloheptylenedia-mine-N,N'-diacetic acid,

N,N'-bis(pyridoxal)-trans-1,2-cyclooctylenediamine-N,N'-diacetic acid,

N,N'-bis(pyridoxal)-1,2-phenylenediamine-N,N'-diacetic acid, and

N,N'-bis(pyridoxal)-cis-1,2-cyclohexylenediamine-N,N'-diacetic acid.

Another group of known paramagnetic metal ion complexes are described in U.S. Pat. No. 4,647,447, together with methods for their manufacture and use. These compounds can be represented by the Formula III.

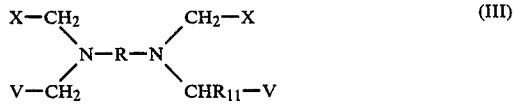

(III)

or

N(CH$_2$X)$_3$ wherein,

X is —COOY, PO$_3$HY or —CONHOY;

Y is a hydrogen atom, a metal ion equivalent and/or a physiologically biocompatible cation of an inorganic or organic base or amino acid;

A is

—CHR$_{12}$—CHR$_{13}$—,

—CH$_2$—CH$_2$(ZCH$_2$—CH$_2$)$_m$,

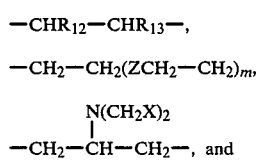

-continued $$-CH_2-CH_2-\overset{\overset{\displaystyle CH_2-CH_2-N(CH_2X)_2}{|}}{N}-CH_2-CH_2-,$$

wherein X is as defined above;
each of $R_{11}$ is hydrogen or methyl;
$R_{12}$ and $R_{13}$ together represent an alkylene group having from 1 to 8 carbons (e.g., trimethylene, tetramethylene, etc.), or individually are hydrogen atoms, lower alkyl groups (e.g., 1–8 carbon atoms), phenyl groups, or benzyl groups;
wherein,
p is 0 or 1;
W is —NN—, —NHCOCH$_2$, NHCOCH$_2$, or —NHCS—;
m represents the number 1, 2 or 3;
Z is an oxygen atom or a sulfur atom or the group $$>NCH_2X \text{ or } >NCH_2CH_2OR_{14},$$

wherein X is as defined above; and
$R_{14}$ is a lower alkyl group (e.g., 1–8 carbon atoms);
V has the same meaning as X, or is —CH$_2$OH or —CONH(CH$_2$)$_n$X, wherein X is as defined above;
n is an integer of from 1 to 1;
or if $R_{11}$, $R_{12}$ and $R_{13}$ are hydrogen atoms, both V's together are the group $$-(CH_2)_w-\overset{\overset{\displaystyle CH_2X}{|}}{N}-CH_2-CH_2-\overset{\overset{\displaystyle CH_2X}{|}}{N}-(CH_2)_w-$$

wherein X is as defined above,
w is the nunber 1, 2 or 3; provided that at least two of the substituents Y represent metal ion equivalents of an element with an atomic number of 21 to 29, 42, 44, 57 to 83.

Included within the compounds of Formula III are the gadolinium chelates of diethylenetriaminepentaacetic acid (DTPA) and its analogs.

Other suitable chelating compounds of Formula III are trans-1,2-cyclohexylenediamine-N,N,N',N'-tetraacetic acid, ethylenedinitrilotetrakis(methanephosphonic acid), 1,4,7,10-tetraazacyclododecane-N,N',N'',N'''-tetraacetic acid, N,N-'bis(1-hydroxybenzyl)ethylenediamine-N,N'-diacetic acid, nitrilo-N,N,N-triacetic acid, 13,23-dioxo-15,18,21-tris(carboxymethyl)-12,15,18,21,24-pentaazapentatriacontanedioic acid, 3,9-bis(1-carboxyethyl)-6-carboxymethyl-3,6,9-triazundecanedioic acid, ethylenediamine-N,N,N',N'-tetraacetic acid, ethylenedinitrilotetra(acethydroxamic acid), 1,10-diaza-4,7-dithiadecane-1,1,10,10-tetraacetic acid, 1,2-diphenylethylenediaminetetraacetic acid, N'-(2-hydroxyethyl)ethylenediamine-N,N,N'-triacetic acid, 1,4,8,11-tetraazacyclotetradecane-N,N',N'',N'''-tetraacetic acid, 1,4,7,10-tetraazacyclododecane-N,N',N''-triacetic acid; diisopropyl iminodiacetic acid, and diethylenetrinitrilopenta(methylphosphonic acid), 1-phenylethylenediaminetetraacetic acid.

Another group of NMRI chelates are the diethylenetriaminepentaacetic acid diamides disclosed in commonly assigned, copending application Ser. No. 671,106 filed Nov. 13, 1984, the entire contents of which are hereby incorporated by reference. These diamides can be represented by Formula IV:

A—DTPA—PM(+Z)     (IV)

wherein,
A—DTPA is a diethylenetriaminepentaacetic acid derivative chelator wherein at least one of the five acetic acid groups is replaced with a functional amide group A;
wherein,
A has the formula:

$$\overset{\overset{\displaystyle O}{\|}}{-C}NH-R_{16}$$

wherein $R_{16}$ is hydrogen or an alkyl group having from 1 to 16 carbons; and
PM(+Z) is a paramagnetic metal ion having an atomic charge of Z, securely chelated into the chelator.

Examples of suitable amides of Formula IV include the diamide, di(methylamide), ethylamide), di(n-propylamide), di(n-butylamide), di(t-butylamide), di(n-pentylamide), di(n-hexylamide), di(heptylamide), di(octylamide), di(nonylamide), di-(decylamide) and amidestearylamide of N,N,N',N'',N''-diethylenetriaminepentaacetic acid.

Another group of NMRI chelates are the diethylenetriaminepentaacetic acid diesters disclosed in commonly assigned, copending application Ser. No. 657,676 filed Oct. 4, 1984, the entire contents of which are hereby incorporated by reference. These compounds are represented by Formula V.

E—DTPA—PM(+Z)     (V)

wherein,
E—DTPA is a diethylenetriaminepentaacetic acid derivative chelator wherein in which at least one of the five acetic acid groups is replaced with a functional ester group E;
wherein,
has the formula:

$$\overset{\overset{\displaystyle O}{\|}}{-C}O-(CH_2)_{(m-1)}-CH_3$$

wherein m is an integer of from 1 to 16; and
PM(+Z) is a paramagnetic metal ion having an atomic charge of Z, securely chelated into the chelator.

Examples of suitable esters of Formula V include the dimethyl, diethyl, di(n-propyl), di(n-butyl), di(t-butyl), di(n-pentyl), di(n-hexyl), diheptyl, dioctyl, dinonyl, didecyl, and methyl-stearyl esters of N,N,N',N'',N''-diethylenetriaminepentaacetic acid.

Other NMRI chelates are disclosed by Valk, J. et al, *BASIC PRINCIPLES OF NUCLEAR MAGNETIC RESONANCE IMAGING*. New York: Elsevier, pp 109–114 (1985). The Valk et al publication also describes the imaging equipment and methods for NMRI, and the entire contents of the Valk et al publication are hereby incorporated by reference in its entirety. Chelates with ethylenediaminetetraacetic acid (EDTA) and DTPA are described. A low toxicity complex is gadolinium-DTPA dimeglumine. Listed ions include $Mn^{2+}$, $Mn^{3+}$, $Fe^{2+}$, $Fe^{3+}$, $Ni^{2+}$, $Cr^{2+}$, $Cu^{2+}$, and the lanthranide series including gadolinium and europium.

Taliaferro, C. et al in "New multidentate ligands. 22. N,N'-dipyridoxyethylenediamine-N,N'-diacetic acid: a new chelating ligand for trivalent metal ions", *Inorg. Chem.* 23: 1188–1192 (1984) describes PLED as a chelating compound for trivalent metal ions. See also U.S. Pat. No. 3,632,637, hereby incorporated by reference in its entirety. Other chelating compounds described are the Fe(III) chelates of N,N'-ethylenebis-2-(o-hydroxyphenyl)glycine (EHPG) and N,N'-bis(1-hydroxybenzyl)ethylenediamine-N,N'-diacetic acid (HBED).

The preferred metal chelates for use in the method of this invention are physiologically acceptable, have in vivo stability and appropriate paramagnetic metal ions.

The paramagnetic metal ion chelates and complexes can be administered in either an oil or aqueous liquid physiologically acceptable media such as described in *REMINGTON'S PHARMACEUTICAL SCIENCES.* 15th Ed., Easton: Mack Publishing Co. pp 1405–1412 and 1461–1487 (1975) and *THE NATIONAL FORMULARY XIV.* 14th Ed. Washington: American Pharmaceutical Association (1975), the contents of which are hereby incorporated by reference. Vehicles developed for injection of opaque materials into the cervix and fallopian tubes in hysterosalpingography procedures can be used, provided they do not contain materials which would increase risk of *S. aureus* infection. Oil systems such as ethiodol (Hom et al, *J. Am. Pharm. Assoc. Sci. Ed.* 46: 254 (1957) can be used.

Alternatively, aqueous systems are suitable. Thickeners have been used in previous experimental contrast media (X-ray, etc.) to retard expulsion from the fallopian tubes and uterus, but with the more rapid imaging possible with NMRI, thickeners are not believed to be necessary. Traditional thickeners are carbohydrate materials which might increase the risk of *S. aureus* infection, and if thickeners are used, they should be selected to be physiologically suitable for use in tubal patency imaging.

Preferred vehicles are neutral saline solutions such as Ringer's Injection, Sodium Chloride Injection, and other carbohydrate-free solutions such as are described in *REMINGTON'S PHARMACEUTICAL SCIENCES* and *THE NATIONAL FORMULARY.* The solutions should be adjusted for pH (most chelates require a slightly acidic medium for long term stability), and be isotonic or iso-osmotic. Preferred solution pH's are within the pH range of from 4 to 8 and preferably within the pH range of 5.5 to 7, optimally below pH 7.

If thickeners are desired, viscous additives such as SALPIX (sodium acetrizoate 53% with polyvinylpyrrolidone, May & Baker, Ltd.) are useful. A variety of low-osmolality contrast media compositions are described by Davies, A. et al, *Clinical Radiology.* 36: 533–536 (1985) including the monoacid dimer of ioxaglate (HERBRIX 320, May & Baker), meglumine isothalamate (CONRAY 280, May & Baker), and the like. The amount of the thickening agent used is determined by the desired viscosity. Thicker viscosities resist expulsion from the fallopian tubes and uterine cavity until imaging is complete, but are unnecessary with the more rapid NMRI imaging techniques. Physiologically acceptable conventional surfactants such as water-soluble cationic, anionic, non-anionic and amphoteric surfactants can be used in the composition to increase wetting properties. Examples of suitable surfactants include polyoxyethylene sorbitan monooleate, polyoxyethylene-polyoxypropylene copolymers, and the like.

The compositions can also contain preservatives, antimicrobial agents, buffers and antioxidants conventionally used with chelate solutions, provided they are physiologically acceptable for introduction into the peritoneal cavity through the cervical cavity and fallopian tubes. All excipients should be compatible with chelates and not interfere with the manufacture, storage and use of the products.

The diagnostic media useful in the method of this invention can contain from 0.0001 to 5.0 moles per liter and preferably from 0.001 to 0.01 moles per liter of the chelate salt or coordination complex of the paramagnetic metal ion. The amount of solution or suspension injected is sufficient to fill the fallopian tubal ducts with the contrast medium (usually less than 10 ml). Generally, dosages of from 0.1 to 15 $\mu M/Kg$ (micromoles per Kg of body weight) are used, assuming that none escapes out through the cervical os during the injection.

Suitable NMRI procedures and equipment are described by Valk, J. et al, supra; Hricak, H., supra; McCarthy, S., supra; and Hamlin, D. et al, supra, the entire contents of the foregoing references being hereby incorporated by reference in their entireties.

The paramagnetic liquids are injected into the uterus by means of a Foley or similar balloon catheter which closes the cervical os to prevent escape of liquid being injected and maintain the slight pressure required to move the liquid through the fallopian tubal ducts. The devices described in U.S. Pat. No. 4,089,337 and by Yoder, I. et al, *AJR.* 133: 335–336 (1979) are suitable provided the devices are manufactured from non-metallic components. The devices include a semi-rigid tubular member for uterine insertion through which fluid can be injected having an inflatable sleeve or balloon on the distal end thereof and with an air line extending along the tubular member to the inflatable sleeve. The tubular member is advanced until the inflatable sleeve is positioned within the uterine cavity, and air is introduced into the sleeve through the air line until it is inflated to a size larger than the cervical os. The balloon retains the injector in place and seals the cervical os, preventing escape of the injection liquid from around its edges and back through the os.

This invention is further illustrated by the following specific but non-limiting examples. Temperatures are given in degrees centigrade and concentrations as weight percents unless otherwise specified. Procedures which are constructively reduced to practice herein are described in the present tense, and procedures which have been carried out in the laboratory are set forth in the past tense.

EXAMPLE 1

Ferrioxamine Concentrations

The signal intensity of ferrioxamine as a function of concentration was determined. The $T_1$ and $T_2$ values were recorded using a RADX spin analyzer operating at 10 MHz. The intensity was calculated according to Mansfield, P. and Morris, P. G., "NMR imaging in biomedicine" in *ADVANCES IN MAGNETIC RESONANCE.* (Ed. Waugh, J. S.), Supplement 2, New York: Academic Press (1982). The TR was set to 130 msec, the TE to 12 msec, theta to 70°, and $T_2^*$ equal to $T_2$. The results are shown in Table A.

TABLE A

| Ferrioxamine mM | $T_1$ (msec) | $T_2$ (msec) | Intensity |
|---|---|---|---|
| 1.41 e$^{-4}$ | 2130 | 675 | 0.296 |
| 7.05 e$^{-4}$ | 712 | 541 | 0.466 |
| 1.41 e$^{-3}$ | 364 | 353 | 0.532 |
| 2.82 e$^{-3}$ | 210 | 195 | 0.570 |
| 5.64 e$^{-3}$ | 110 | 93 | 0.634 |
| 8.46 e$^{-3}$ | 69 | 59 | 0.671 |
| 1.13 e$^{-2}$ | 50 | 42 | 0.663 |
| 1.41 e$^{-2}$ | 40 | 30 | 0.611 |
| 1.69 e$^{-2}$ | 34 | 27 | 0.592 |
| 1.97 e$^{-2}$ | 32 | 25 | 0.574 |
| 2.25 e$^{-2}$ | 27 | 19 | 0.497 |
| 2.54 e$^{-2}$ | 23 | 19 | 0.498 |
| 2.82 e$^{-2}$ | 26 | 16 | 0.442 |
| 3.10 e$^{-2}$ | 23 | 15 | 0.421 |
| 3.38 e$^{-2}$ | 18 | 13 | 0.373 |
| 3.66 e$^{-2}$ | 19 | 13 | 0.373 |

Intensities greater then 0.5 are preferred, corresponding to a concentration range of from $1\times10^{-3}$ to $2.5\times10^{-2}$ mM of ferrioxamine with a maximum intensity at about 8.5 mM.

EXAMPLE 2

Ferrioximine Imaging A solution of 200 mg/ml of ferrioxamine in a sterile, pyrogen-free solution is prepared. One ml (200 mg) of this solution is diluted into 100 ml of Ringer's Injection USP. The diluted ferrioxamine solution is delivered through a Harris Uterine Injector (United International Marketing Resources) into the cervical cavity until patients experience pressure or until a maximum of 10 ml is delivered. Following instillation, the imaging parameters and NMR instrument settings (TR, TE, and flip angle) are selected to maximize the definition of the fallopian tube surfaces between the white image of the solution and the dark image of the cervix and fallopian tube wall, and images are obtained for examination of the fallopian tubal ducts and their surfaces for deformation or occlusion which might interfere with the movement of fertilized ovum to the uterus.

EXAMPLE 3

MnDPDP Concentrations

Repeating the procedure of Example 1 with the sodium-calcium Mn(II) chelate of N,N'-bis-(pyridoxal-5-phosphate)ethylenediamine-N,N'-diacetic acid (MnDPDP) yields the intensities shown in Table B.

TABLE B

| MnDPDP, mM | $T_1$ (msec) | $T_2$ (msec) | Intensity |
|---|---|---|---|
| 1.00 e$^{-2}$ | 47 | 38 | 0.65 |
| 5.00 e$^{-3}$ | 78 | 78 | 0.68 |
| 2.50 e$^{-3}$ | 167 | 166 | 0.60 |
| 1.25 e$^{-3}$ | 335 | 289 | 0.52 |
| 6.25 e$^{-4}$ | 584 | 538 | 0.50 |
| 3.13 e$^{-4}$ | 997 | 637 | 0.43 |
| 1.56 e$^{-5}$ | 1570 | 627 | 0.34 |
| 7.81 e$^{-5}$ | 1850 | 727 | 0.33 |
| 3.91 e$^{-5}$ | 2230 | 664 | 0.29 |
| 1.95 e$^{-5}$ | 2680 | 549 | 0.23 |

Concentration greater than 6.25 e$^{-4}$ mM up to the toxicity limits of MnDPDP are suitable.

EXAMPLE 4

MnPLED Concentrations

Repeating the procedure of Example 1 with the sodium-calcium Mn(II) chelate of N,N'-di(pyridoxyl)ethylenediamine-N,N'-diacetic acid (MnPLED) yields the intensities shown in Table C.

TABLE C

| MnPLED, mM | $T_1$ (msec) | $T_2$ (msec) | Intensity |
|---|---|---|---|
| 1.00 e$^{-2}$ | 26 | 10 | 0.28 |
| 5.00 e$^{-3}$ | 67 | 21 | 0.48 |
| 2.50 e$^{-3}$ | 111 | 39 | 0.53 |
| 1.25 e$^{-3}$ | 219 | 81 | 0.47 |
| 6.25 e$^{-4}$ | 377 | 145 | 0.41 |

Concentration from 5.00 e$^{-3}$ up to 1.25 e$^{-3}$ mM of MnPLED are suitable.

EXAMPLE 5

MnEDTP Concentrations

Repeating the procedure of Example 1 with the tetra-N-methylglucamine salt of Mn(II) complex of ethylenedinitrilotetrakis(methanephosphonic acid) (MnEDTP) yields the intensities shown in Table D.

TABLE D

| MnEDTP, mM | $T_1$ (msec) | $T_2$ (msec) | Intensity |
|---|---|---|---|
| 1.00 e$^{-2}$ | 31 | 19 | 0.49 |
| 5.00 e$^{-3}$ | 41 | 37 | 0.65 |
| 2.50 e$^{-3}$ | 83 | 74 | 0.66 |
| 1.25 e$^{-3}$ | 159 | 123 | 0.58 |

Concentration from MnEDTP over the full range shown in the table are suitable.

EXAMPLE 6

GdDTPA Concentrations

Repeating the procedure of Example 1 with the Gd(III) complex of diethylenetriamine-N,N,N',N'',N''-pentacetic acid (GdDTPA) yields the intensities shown in Table E.

TABLE E

| GdDTPA, mM | $T_1$ (msec) | $T_2$ (msec) | Intensity |
|---|---|---|---|
| 6.25 e$^{-3}$ | 40 | 35 | 0.64 |
| 3.13 e$^{-3}$ | 83 | 76 | 0.67 |
| 1.56 e$^{-3}$ | 163 | 155 | 0.60 |

Concentration from GdDTPA over the full range shown in the table are suitable.

EXAMPLE 6

MnDCTA Concentrations

Repeating the procedure of Example 1 with the disodium salt of manganese(II) complex of trans-1,2-cyclohexylenediamine-N,N,N',N'-tetraacetic acid (MnDCTA) yields the intensities shown in Table F.

TABLE F

| MnDCTA, mM | $T_1$ (msec) | $T_2$ (msec) | Intensity |
|---|---|---|---|
| 1.00 e$^{-2}$ | 32 | 22 | 0.54 |
| 5.00 e$^{-3}$ | 55 | 43 | 0.66 |
| 2.50 e$^{-3}$ | 95 | 69 | 0.64 |
| 1.25 e$^{-3}$ | 171 | 126 | 0.57 |

Concentration from MnDCTA over the full range shown in the table are suitable.

EXAMPLE 8

Other Chelating Agent Concentrations

Repeating the procedure of Example 1 with sodium-calcium Mn(II) chelate of N,N'-bis-(pyridoxal-5-phosphate)-trans-1,2-cyclohexylenediamine-N,N'-diacetic acid (MnDPCP) yields results substantially the same as shown in Table B.

Repeating the procedure of Example 1 with ferric N,N-'bis(1-hydroxybenzyl)ethylenendiamine-N,N'diacetic acid (FeHBED) and ferric N,N'ethylenebis-2-(2-hydroxyphenyl)glycine (FeEHPG) yields results substantially the same as shown in Table A.

Repeating the procedure of Example 1 with the tetra-N-methylglucamine salt of GD(III) complex of ethylenedinitrilo-tetrakis(methanephosphonic acid) (GdEDTP), the sodium salt of the Gd(III) complex of 1,4,7,10-tetraazacyclododecane-N,N',N'',N'''-tetraacetic acid (GdDOTA), the Gd(III) complexes of the diamide derivatives of DTPA, and the Gd(III) complexes of the diester derivatives of DTAP yields, for each compound, results substantially the same as shown in Table E.

EXAMPLE 9

Imaging with Other Chelates

Repeating the procedure of Example 2 with the optimum concentrations of the chelates listed in Examples 3, 4, 5, 6, 7 and 8 in Ringer's Injection solution provides detailed images of the fallopian tubes.

We claim:

1. A method for determining fallopian tubal patency comprising injecting a physiologically acceptable liquid contrast medium containing a resolution enhancing concentration of a compatible paramagnetic metal ion complexed with a chelating agent, into a fallopian tubal duct and exposing the fallopian tubal duct to an NMR measuring step to which the contrast medium is responsive, thereby imaging the fallopian tubal duct, wherein the chelating agent is a dipyridoxyl phosphate compound of Formula I:

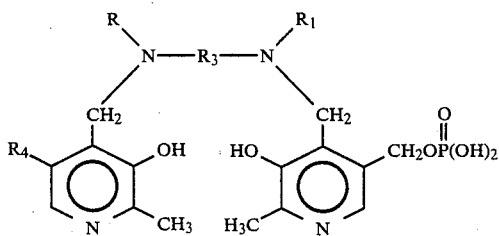

wherein
R is hydrogen or

$R_1$ is hydrogen or

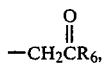

and one of R and $R_1$ is other than hydrogen;

$R_3$ is alkylene having from 1 to 8 carbons, 1,2-cycloalkylene having from 5 to 8 carbons, or 1,2-arylene having from 6 to 10 carbons, or $R_4$ is hydrogen, hydroxymethyl, alkyl having from 1 to 6 carbons or

$R_5$ and $R_6$ are each, individually, hydroxy, alkoxy having from 1 to 18 carbons, hydroxy-substituted alkoxy havig from 1 to 18 carbons, amino having from 1 to 18 carbons;

the phosphate group mono and diesters of the compounds thereof with monohydric and polyhydric alcohols having from 1 to 18 carbons, or alkylamino alcohols, each having from 1 to 18 carbons, and the salts thereof.

2. The method of claim 1 wherein R is

and $R_1$ is

3. The method of claim 2 wherein $R_5$ and $R_6$ are each, individually, hydroxy, alkoxy having from 1 to 8 carbons, amino having from 1 to 8 carbons.

4. The method of claim 3 wherein $R_5$ and $R_6$ are hydroxy or a salt thereof.

5. The method of claim 4 wherein the chelating agent is
N,N'-(dipyridoxyl-5-phosphate)alkylendiamine-N,N'-diacetic acid or
N,N'-(dipyridoxyl-5-phosphate)-1,2-cycloalkylenediamine-N,N'-diacetic acid.

6. The method of claim 5 wherein the paramagnetic metal ion is Fe(III), Mn(II) or Gd(III) and the chelating agent is N,N'-(dipyridoxyl-5-phosphate)ethylenediamine-N,N'-diacetic acid.

7. The method of claim 5, wherein the paramagnetic metal ion is Fe(III), Mn(II) or Gd(III) and the chelating agent is N,N'-(dipyridoxyl-5-phosphate)trans-1,2-cyclohexylenediamine-N,N'-diacetic acid.

8. A method for determining fallopian tubal patency comprising injecting a physiologically acceptable liquid contrast medium containing a resolution enhancing concentration of a compatible paramagnetic metal ion complexed with a chelating agent, into a fallopian tubal duct and exposing the fallopian tubal duct to an NMR measuring step to which the contrast medium is responsive, thereby imaging the fallopian tubal duct, wherein the chelating agent is a dipyridoxyl phosphate compound of Formula II

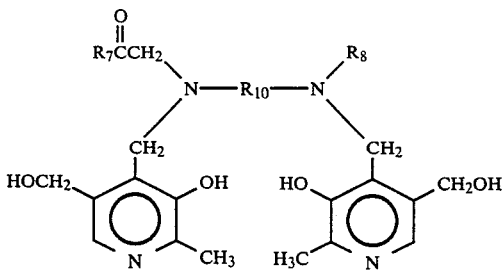 (II)

wherein

R<sub>7</sub> is hydroxy, alkoxy having from 1 to 18 carbons, hydroxy-substituted alkoxy having from 1 to 18 carbons, amino having from 1 to 18 carbons;

R<sub>8</sub> is hydrogen or

R<sub>9</sub> is hydroxy, alkoxy having from 1 to 18 carbons, amino having from 1 to 18 carbons; and R<sub>10</sub> is alkylene having from 1 to 8 carbons, 1,2-cycloalkylene having from 5 to 8 carbons, or 1,2-arylene having from 6 to 10 carbons; and the pharmaceutically acceptable water-soluble salts thereof.

9. The method of claim 8 wherein the paramagnetic metal ion is Fe(III), Mn(II) or Gd(III) and the chelating agent is N,N'-(dipyridoxyl)alkylenediamine-N,N'-diacetic acid or N,N'-(dipyridoxyl)-1,2-cycloalkylenediamine-N,N'-diacetic acid.

10. The method of claim 9 wherein the paramagnetic metal ion is Mn(II), Fe(III) or Gd(III) and the chelating agent is N,N'-(dipyridoxyl)ethylenediamine-N,N'-diacetic acid.

* * * * *